United States Patent
Aloup et al.

[11] Patent Number: 5,672,705
[45] Date of Patent: Sep. 30, 1997

[54] IMIDAZO (1,2-A)PYRAZINE-4-ONE DERIVATIVES/USEFUL AS ANTAGONISTS OF AMPA AND NMDA RECEPTORS

[75] Inventors: Jean-Claude Aloup, Villeneuve le Roi; Serge Mignani, Chatenay-Malabry, both of France

[73] Assignee: Rhone-Poulenc Rorer S.A., Antony, France

[21] Appl. No.: 583,036

[22] PCT Filed: Jul. 11, 1994

[86] PCT No.: PCT/FR94/00865
§ 371 Date: Jan. 16, 1996
§ 102(e) Date: Jan. 16, 1996

[87] PCT Pub. No.: WO95/02602
PCT Pub. Date: Jan. 26, 1995

[30] Foreign Application Priority Data

Jul. 16, 1993 [FR] France ................. 93 08753

[51] Int. Cl.[6] ................................. C07D 241/36
[52] U.S. Cl. ........................... 544/343; 514/249
[58] Field of Search ................ 544/343; 514/249

[56] References Cited

U.S. PATENT DOCUMENTS 5,182,279 1/1993 Jorgensen et al. ............... 514/250

OTHER PUBLICATIONS

McQuaid et al., "Synthesis and Excitatory Amino Acid Pharmacology of a Series of Heterocyclic-Fused Quinoxalinones and Quinazolines", Journal of Medicinal Chemistry, 35(18):3319-3324 (1992).

*Primary Examiner*—Matthew V. Grumbling
*Assistant Examiner*—Michael Bucknum
*Attorney, Agent, or Firm*—Finnegan, Henderson, Farabow, Garrett & Dunner, L.L.P.

[57] ABSTRACT

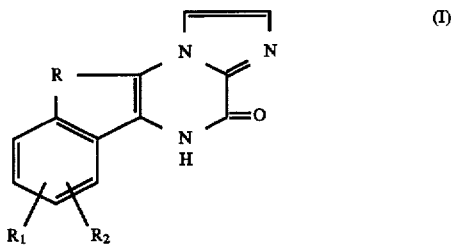

Compounds of formula (I), wherein R is an oxygen or sulphur atom or an NH or N-alk radical, and each of $R_1$ and $R_2$, which are the same or different, is a hydrogen or halogen atom or an alkyl, alkoxy, amino, acylamino, —NH—CO—NH—Ar,—N=CH—N(alk)alk', nitro, cyano, phenyl, imidazolyl or $SO_3H$ radical, the preparation thereof, and drugs containing such compounds, are disclosed.

5 Claims, No Drawings

IMIDAZO (1,2-A)PYRAZINE-4-ONE DERIVATIVES/USEFUL AS ANTAGONISTS OF AMPA AND NMDA RECEPTORS

This application is a 371 of PCT/FR94/00865 dated Jul. 11, 1994 published as WO95/02602 Jan. 26, 1995.

The present invention relates to the compounds of formula:

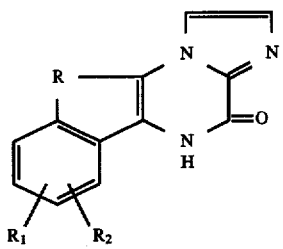

(I)

to their salts, to their preparation and to the medicaments containing them.

In the formula (I),

R represents an oxygen or sulphur atom or an NH or N-alk radical, $R_1$ and $R_2$, which are identical or different, represent hydrogen or halogen atoms or alkyl, alkoxy, amino, acylamino, —NH—CO—NH—Ar, —N=CH—N(alk)alk', nitro, cyano, phenyl, imidazolyl or $SO_3H$ radicals, Ar represents a phenyl radical, alk represents an alkyl radical, alk' represents an alkyl radical which is identical to or different from alk.

In the preceding and following definitions, except when otherwise mentioned, the alkyl and alkoxy radicals contain 1 to 4 carbon atoms in a straight or branched chain, the acyl radicals and portions contain 2 to 5 carbon atoms and the halogen atoms are chosen from fluorine, chlorine, bromine and iodine.

The compounds of formula (I) in which $R_1$ and/or $R_2$ represent an —N|CH—N(alk)alk' radical have isomeric forms (E and Z). These isomers and their mixtures form part of the invention.

The compounds of formula (I) in which R represents an oxygen atom can be prepared by dealkylation, dehydration and desalification of the derivatives of formula:

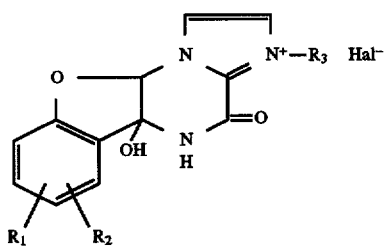

(II)

in which $R_1$ and $R_2$ have the same meanings as in the formula (I), $R_3$ represents an alkyl radical and Hal represents a halogen atom. Hal preferably represents a bromine atom.

This reaction is preferably carried out in the presence of imidazole, by heating at a temperature between 100° and 200° C.

The derivatives of formula (II) can be obtained by reacting the 1-alkyl-1H-imidazole-2-carboxamide with a derivative of formula:

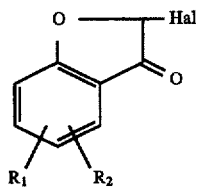

(III)

in which $R_1$ and $R_2$ have the same meanings as in the formula (I) and Hal represents a halogen atom. Hal preferably represents a bromine atom.

This reaction is generally carried out in an inert solvent, such as acetonitrile, at the boiling temperature of the reaction mixture.

1-Alkyl-1H-imidazole-2-carboxamides can be obtained by application or adaptation of the method described by D. D. Davey, J. Org. Chem., 52, 4379 (1987).

The derivatives of formula (III) can be obtained by halogenation of the corresponding 3-coumaranones, by means of a halogenating agent, in an inert solvent such as a chlorinated solvent (methylene chloride or chloroform, for example), at a temperature in the range of −15° C. Bromine or chlorine is preferably used.

3-Coumaranones are marketed or can be obtained by application or adaptation of the method described by A. R. Deshpande et al., Synth. Commun., 20 (6), 809 (1990) and G. Schenk et al., Tetrahedron Lett., (19), 2375 (1968).

The compounds of formula (I) in which R represents a sulphur atom can be prepared by cyclization of a derivative of formula:

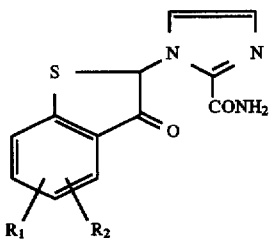

(IV)

in which $R_1$ and $R_2$ have the same meanings as in the formula (I).

This cyclization is generally carried out by means of an acid such as hydrochloric acid in aqueous solution, at a temperature in the region of 20° C.

The derivatives of formula (IV) can be obtained by reacting ammonia with a derivative of formula:

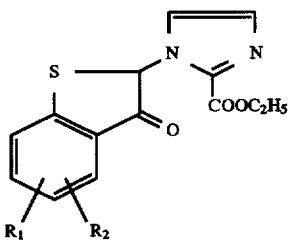

(V)

in which $R_1$ and $R_2$ have the same meanings as in the formula (I).

This reaction is generally carried out in an inert solvent, such as an alcohol, at a temperature between 20° C. and the boiling temperature of the reaction mixture.

The derivatives of formula (V) can be obtained by condensation of ethyl imidazole-2-carboxylate with a derivative of formula:

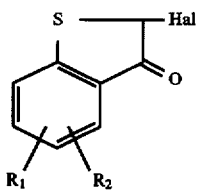

(VI)

in which $R_1$ and $R_2$ have the same meanings as in the formula (I) and Hal represents a halogen atom and preferably a bromine atom.

This reaction is carried out in an inert solvent, such as an alcohol (methanol or ethanol, for example), at the boiling temperature of the reaction mixture.

Ethyl imidazole-2-carboxylate can be obtained according to the method described in U.S. Pat. No. 3,600,399.

The derivatives of formula (VI) can be obtained by application or adaptation of the method described by Z. I. Miroshnichenko and M. A. Al'Perovich, J. Gen. Chem. USSR, 32, 1218 (1962).

The compounds of formula (I) in which R represents an NH radical can be prepared by hydrolysis of a derivative of formula:

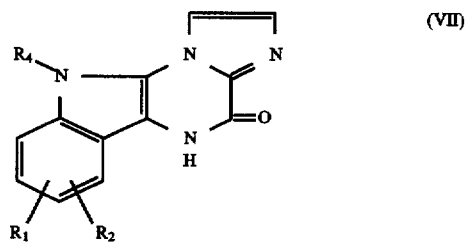

(VII)

in which $R_1$ and $R_2$ have the same meanings as in the formula (I) and $R_4$ represents a (2–5 C) acyl radical.

This reaction is carried out in an inert solvent such as an amide (dimethylformamide, for example), water or a mixture of these solvents, at a temperature varying from 5° C. to the boiling temperature of the reaction mixture.

The derivatives of formula (VII) in which $R_4$ represents a (2–5 C) acyl radical can be obtained by cyclization of the derivatives of formula:

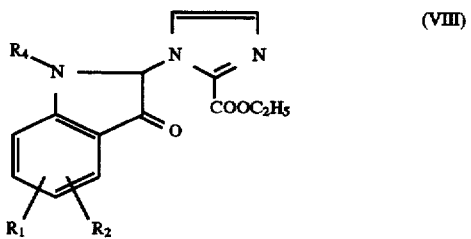

(VIII)

in which $R_1$ and $R_2$ have the same meanings as in the formula (I) and $R_4$ represents a (2–5 C) acyl radical.

This cyclization is preferably carried out in an inert solvent, such as acetic acid, in the presence of ammonium acetate, at the boiling temperature of the reaction mixture.

The derivatives of formula (VIII) can be obtained by heating ethyl imidazole-2-carboxylate and a derivative of formula:

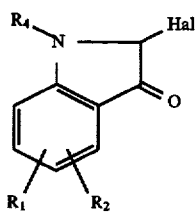

(IX)

in which $R_1$ and $R_2$ have the same meanings as in the formula (I), $R_4$ represents a (2–5 C) acyl radical and Hal represents a halogen, and preferably bromine, atom, at a temperature in the range of 120° C.

The derivatives of formula (IX) can be obtained by application or adaptation of the method described by V. S. Velezheva et al., Khim. Farm. Zh., 24 (12), 46 (1990).

The compounds of formula (I) in which R represents an N-alk radical can be prepared by alkylation of a corresponding compound of formula (I) in which R represents an NH radical.

This reaction is preferably carried out by means of an alkyl halide, in the presence of an organic base such as triethylamine or an inorganic base such as an alkali metal hydroxide (sodium hydroxide or potassium hydroxide, for example) or an alkali metal carbonate (sodium carbonate, for example), optionally in the presence of tetrabutylammonium bromide, in an inert solvent such as dimethyl sulphoxide, dimethylformamide or pyridine, at a temperature between 20° and 50° C.

The compounds of formula (I) can be purified by the usual known methods, for example by crystallization, chromatography or extraction.

The E and Z isomers of the compounds of formula (I) in which $R_1$ and/or $R_2$ represent an —N|CH—N(alk)alk' radical can be separated by the usual known methods, for example by crystallization or chromatography.

The compounds of the formula (I) containing a basic residue can optionally be converted to addition salts with an inorganic or organic acid by the action of such an acid in an organic solvent such as an alcohol, a ketone, an ether or a chlorinated solvent.

The compounds of formula (I) containing an acid residue can optionally be converted to metal salts or to addition salts with nitrogenous bases according to methods known per se. These salts can be obtained by reacting a metal base (alkali metal or alkaline-earth metal, for example), ammonia, an amine or a salt of an amine with a compound of formula (I), in a solvent. The salt formed is separated by the usual methods.

These salts also form part of the invention.

There may be mentioned, as examples of pharmaceutically acceptable salts, the addition salts with inorganic or organic acids (such as acetate, propionate, succinate, benzoate, fumarate, maleate, oxalate, methanesulphonate, isethionate, theophyllineacetate, salicylate, methylenebis (β-hydroxynaphthoate), hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, benzylamine, N-benzyl-β-phenethylamine, choline, arginine, leucine, lysine or N-methylglucamine).

The compounds of formula (I) exhibit advantageous pharmacological properties. These compounds are antagonists of the α-amino-3-hydroxy-5-methyl-4-isoxazolepropionic acid (AMPA) receptor, also known under the name of the quisqualate receptor.

Moreover, the compounds of formula (I) are non-competitive antagonists of the N-methyl-D-aspartate (NMDA) receptor and, more particularly, they are ligands for the glycine-modulatory sites of the NMDA receptor.

These compounds are thus useful for treating or preventing all ischaemias (such as focal or global ischaemia) resulting from cerebrovascular accidents, a cardiac arrest, arterial hypotension, a heart or pulmonary surgical operation or severe hypoglycaemia. They are also useful in the treatment of effects due to anoxia, whether perinatal or resulting from drowning or cerebrospinal lesions. These compounds can also be used for treating and preventing the development of neurodegenerative diseases, Huntington's chorea, Alzheimer's disease, amyotrophic lateral sclerosis, olivopontocerebellar atrophy and Parkinson's disease. These compounds can also be used with respect to epileptogenic and/or convulsive symptoms, for the treatment of cerebral or spinal traumas, traumas related to generation of the inner ear (R. Pujol et al., Neuroreport, 3, 299–302 (1992)) or of the retina (J. L. Monsinger et al., Exp. Neurol., 113, 10–17 (1991)), of anxiety (Kehne et al., Eur. J. Pharmacol., 193, 283 (1991)), of depression (Trullas et al., Eur. J. Pharmacol., 185, 1 (1990)), of schizophrenia (Reynolds, TIPS, 13, 116 (1992)), of Tourette's syndrome and of hepatic encephalopathies, as analgesics (Dickenson et al., Neurosc. Letters, 121, 263 (1991)), antiinflammatories (Sluta et al., Neurosci. Letters, 149, 99–102 (1993)), antianorexics (Sorrels et al., Brain Res., 572, 265 (1992)), antimigraines and antiemetics, and for treating poisonings by neurotoxins or other agonist substances of the NMDA receptor, and neurological disorders associated with viral diseases such as AIDS (Lipton et al., Neuron, 7, 111 (1991)), rabies, measles and tetanus (Bagetta et al., Br. J. Pharmacol., 101, 776 (1990)). These compounds are also useful for preventing symptoms of withdrawal from drugs and from alcohol and inhibiting addiction to the dependence on opiates. They can also be used in the treatment of deficiencies related to mitochondrial anomalies such as mitochondrial myopathy, Leber's syndrome, Wernicke's encephalopathy, Rett's syndrome, homocysteinaemia, hyperprolinaemia, hydroxybutiricaminoaciduria, lead encephalopathy and sulphite oxidase deficiency.

The affinity of the compounds of formula (I) with respect to the AMPA receptor was determined by studying the antagonism of the specific binding of [$^3$H]-AMPA on rat cerebral cortex membranes (Honoré et al., Neuroscience Letters, 54, 27 (1985)). The [$^3$H]-AMPA is incubated in the presence of 0.2 mg of proteins at 4° C. for 30 minutes in 10 mM KH$_2$PO$_4$, 100 mM KSCN, pH 7.5 buffer. The non-specific binding is determined in the presence of 1 mM L-glutamate. The bonded radioactivity is separated by filtration on Pharmacia filters (Printed Filtermate A). The inhibiting activity of these products is equal to or less than 100 µM.

The affinity of the compounds of formula (I) for the glycine site linked to the NMDA receptor was determined by studying the antagonism of the specific binding of [$^3$H]-DCKA on rat cerebral cortex membranes according to the method described by T. Canton et al., J. Pharm. Pharmacol., 44, 812 (1992). The [$^3$H]-DCKA (20 nM) is incubated in the presence of 0.1 mg of proteins at 4° C. for 30 minutes in 50 mM, pH 7.5, HEPES buffer. The non-specific binding is determined in the presence of 1 mM glycine. The bonded radioactivity is separated by filtration on Whatman GF/B filters. The inhibiting activity of these products is equal to or less than 100 µM.

The compounds of formula (I) have a low toxicity. Their LD$_{50}$ in mice is greater than 50 mg/kg by the IP route.

The compounds of formula (I) in which R$_1$ and R$_2$ represent hydrogen atoms and R represents an oxygen or sulphur atom or an NH or N-alk radical are particularly advantageous.

EXAMPLE 1

A solution of 6 g of 5a-hydroxy-3-methyl-4-oxo-5a,10a-dihydro-5H-benzofuro[3,2-e]imidazo-[1,2-a]pyrazinium bromide in 30 g of molten imidazole is heated for 4 hours at 155° C., retained after cooling for 15 hours at a temperature in the region of 20° C. and then again heated for 6 hours at 165° C. and for 2 hours at 175° C. The mixture is cooled to a temperature in the region of 100° C. and, after slow addition of 50 ml of distilled water, poured onto 250 ml of distilled water, cooled to 20° C. and filtered. The filtrate is concentrated to one sixteenth of its volume under reduced pressure (15 mm Hg; 2 kPa) at 60° C. and cooled to 20° C. The solid is separated by filtration and dried under reduced pressure (15 mm Hg; 2 kPa) at 20° C. The product obtained (1.4 g) is dissolved in 120 ml of boiling acetic acid and the solution to which 0.1 g of decolouring charcoal is added, is filtered while hot and cooled to 20° C. The crystals are separated by filtration, washed twice with a total of 100 ml of ethanol and with 50 ml of ethyl ether and then dried under reduced pressure (1 mm Hg; 0.13 kPa) at 80° C. There is thus obtained 0.8 g of 5H-benzofuro-[3,2-e]imidazo[1,2-a]pyrazine-4-one, subliming from 320° C. [N.M.R. spectrum: (300 MHz, d$_6$-DMSO, δ in ppm): 7.45 (limit ab, 2H, —H7 and —H8), 7.68 and 8.27 (2 s, each 1H, imidazole —H), 7.78 and 7.92 (2 mt, each 1H, H6 and —H9), 12.42 (unresolved peak, 1H, —NH—)].

5a-Hydroxy-3-methyl-4-oxo-5a,10a-dihydro-5H-benzofuro[3,2-e]imidazo[1,2-a]pyrazinium bromide can be prepared in the following way: a solution of 6 g of 2-bromo-2H-benzofuran-3-one in 20 ml of acetonitrile is added to a boiling solution of 1-methyl-1H-imidazole-2-carboxamide in 30 ml of acetonitrile. The mixture is stirred for 8 hours at boiling point and, after cooling to 20° C., the crystals are separated by filtration, washed twice with a total of 50 ml of acetone and 50 ml of ethyl ether and then dried under reduced pressure (15 mm Hg; 2 kPa) at 20° C. There are thus obtained 6.7 g of 5a-hydroxy-3-methyl-4-oxo-5a,10a-dihydro-5H-benzofuro[3,2-e]imidazo[1,2-a]pyrazinium bromide [N.M.R. spectrum: (200 MHz, d$_6$-DMSO, δ in ppm): 4.15 (s, 3H, N$^+$—CH3), 6.74 (s, 1H, CH), 7.08 and 7.60 (2 d, J=7.5 Hz, each 1H, —H6 and —H9), 7.18 and 7.45 (2 t, J=7.5 Hz, 2H, —H7 and —H8), 8.15 and 8.25 (2 d, J=1 Hz, each 1H, imidazole —H).

2-Bromo-2H-benzofuran-3-one can be prepared in the following way: 18.4 g of bromine are added to a solution, maintained at −10° C., of 31.7 g of 2H-benzofuran-3-one in 460 ml of methylene chloride. After stirring for 30 minutes, 18.4 g of bromine are again added and the mixture is stirred for 2 hours 30 minutes at the same temperature, neutralized with 100 ml of a saturated aqueous sodium hydrogencarbonate solution, washed with 100 ml of a saturated aqueous sodium chloride solution, dried over anhydrous magnesium sulphate and concentrated to dryness under reduced pressure (15 mm Hg; 2 kPa) at 45° C. There are thus obtained 46.8 g of 2-bromo-2H-benzofuran-3-one, melting at 60° C.

1-Mehyl-1H-imidazole-2-carboxamide can be prepared according to the process described by D. D. Davey, J. Org. Chem., 52, 4379 (1987).

EXAMPLE 2

1 g of 1-(3-oxo-2,3-dihydrobenzo[b]thiophene-2-yl) imidazole-2-carboxamide is dissolved in 50 ml of a 10N aqueous hydrochloric acid solution and, after stirring for 10 minutes at 20° C., the crystals are separated by filtration, washed twice with a total of 10 ml of distilled water and with 5 ml of acetone and then dried under reduced pressure (1 mm Hg; 0.15 kPa) at 100° C. There is thus obtained 0.61 g of 5H-[1]benzothieno[3,2-e]imidazo[1,2-a]pyrazine-4-one hydrochloride (0.4 mol of acid per mole of base), decomposing without melting at around 320° C. [N.M.R. spectrum: (300 MHz, d$_6$-DMSO, δ in ppm): 7.52 and 7.58 (2 dt, J=7.5 and 1 Hz, each 1H, —H7 and —H8), 7.78 and 8.35 (2 broad s, each 1H, imidazole —H), 8.15 and 8.36 (2 broad d, each 1H, —H6 and —H9), 12.92 (unresolved peak, 1H, —NH—)].

1-(3-Oxo-2,3-dihydrobenzo[b]thiophene-2-yl)imidazole-2-carboxamide can be prepared in the following way: a solution of 1.92 g of ethyl 1-(3-oxo-2,3-dihydrobenzo[b]thiophene-2-yl)imidazole-2-carboxylate in 130 ml of a 5N methanolic ammonia solution is stirred for 15 hours at a temperature in the region of 20° C. and then concentrated to dryness under reduced pressure (15 mm Hg; 2 kPa) at 40° C. The product obtained (1.66 g) is suspended in 30 ml of isopropyl ether, filtered, washed twice with a total of 10 ml of isopropyl ether and dried under reduced pressure (15 mm Hg; 2 kPa) at 20° C. There are thus obtained 1.5 g of 1-(3-oxo-2,3-dihydrobenzo[b]thiophene-2-yl)imidazole-2-carboxamide, melting at 180° C.

Ethyl 1-(3-oxo-2,3-dihydrobenzo[b]thiophene-2-yl)imidazole-2-carboxylate can be prepared in the following way: 18 g of 2-bromo-2H-benzo[b]thiophene-3-one are added at 50° C. to a solution of 20.1 g of ethyl imidazole-2-carboxylate in 500 ml of ethanol. The mixture is heated at boiling point for 10 hours, cooled to 20° C., filtered and the filtrate is concentrated to dryness under reduced pressure (15 mm Hg; 2 kPa) at 50° C. The product obtained is chromatographed on 2.7 kg of neutral silica gel (0.020–0.045 mm) contained in a column with a diameter of 9 cm, elution being carried out under pressure with a methylene chloride/ethyl acetate (80/20 by volume) mixture and 1 liter fractions being collected. The fractions containing the expected product are concentrated to dryness under reduced pressure (15 mm Hg; 2 kPa) at 50° C. and the product obtained (3.4 g ) is suspended in 50 ml of petroleum ether, filtered, washed with 10 ml of petroleum ether and dried while exposed to the air. There are thus obtained 3.2 g of ethyl 1-(3-oxo-2,3-dihydrobenzo[b]thiophene-2-yl)imidazole-2-carboxylate, melting at 174° C.

2-Bromo-2H-benzo[b]thiophene-3-one can be prepared as described by Z. I. Miroshnichenko and M. A. Al'Perovich, J. Gen. Chem. USSR, 32, 1218 (1962).

EXAMPLE 3

0.45 g of 5H,10H-imidazo[1,2-a]indolo[3,2-e]-pyrazine-4-one is dissolved at 60° C. in 50 ml of dimethyl sulphoxide and the solution is cooled to 20° C. 0.010 g of tetrabutylammonium bromide, 0.8 g of sodium hydroxide and 0.3 g of ethyl iodide are then added. The mixture is stirred for 60 hours at a temperature in the region of 20° C., poured onto 400 ml of distilled water and acidified with 15 ml of acetic acid. The insoluble material is separated by filtration, washed with distilled water to neutrality and dried under reduced pressure (5 mm Hg; 0.75 kPa) at 60° C. The product obtained (0.3 m) is chromatographed on 20 g of neutral silica gel (0.020–0.045 mm) contained in a column with a diameter of 2 cm, elution being carried out under pressure with a methylene chloride/methanol (90/10 by volume) mixture. The fractions containing the most polar product are concentrated to dryness under reduced pressure (15 mm Hg; 2 kPa) at 50° C. The product obtained (120 mg) is suspended twice in a total of 20 ml of methanol, filtered and dried under reduced pressure (1 mm Hg; 0.13 kPa) at 60° C. There is thus obtained 0.03 g of 10-ethyl-5H,10H-imidazo[1,2-a]-indolo[3,2-e]pyrazine-4-one, melting at 315° C.

EXAMPLE 4

2 g of 10-acetyl-5H,10H-imidazo[1,2-a]-indolo[3,2-e]pyrazine-4-one are dissolved in 200 ml of boiling dimethylformamide and the solution, to which decolouring charcoal is added, is filtered while hot, diluted with 50 ml of distilled water, cooled and retained for 16 hours at 5° C. The crystals are separated by filtration, washed 3 times with a total of 60 ml of distilled water and 3 times with a total of 60 ml of acetone and then dried under reduced pressure (1 mm Hg; 0.15 kPa) at 100° C. There are thus obtained 1.3 g of 5H,10H-imidazo[1,2-a]indolo[3,2-e]pyrazine-4-one, which decomposes without melting above 300° C. [N.M.R. spectrum: (200 MHz, d$_6$-DMSO, δ in ppm): 7.20 and 7.30 (2 t, J=7.5 Hz, 2H, —H7 and —H8), 7.67 and 8.12 (2 broad s, each 1H, imidazole —H), 7.58 and 7.93 (2 d, J=7.5 Hz, each 1H, —H7 and —H9), 12.00 to 12.70 (unresolved peak, 2H, —NH)].

10-Acetyl-5H,10H-imidazo[1,2-a]indolo-[3,2-e]pyrazine-4-one can be prepared in the following way: a solution of 8.4 g of ethyl 1-(1-acetyl-3-oxo-2-indolinyl)imidazole-2-carboxylate and 206 g of ammonium acetate in 300 ml of acetic acid is heated at boiling point for 1 hour, cooled to a temperature in the region of 20° C. and treated with 50 ml of distilled water. The crystals are separated by filtration, washed twice with a total of 100 ml of distilled water and with 20 ml of acetone and then dried under reduced pressure (5 mm Hg; 0.65 kPa) at 60° C. There are thus obtained 5.6 g of 10-acetyl-5H,10H-imidazo[1,2-a]indolo[3,2-e]pyrazine-4-one, melting at 340° C.

Ethyl 1-(1-acetyl-3-oxo-2-indolinyl)-imidazole-2-carboxylate can be prepared in the following way: a molten mixture of 10.2 g of 1-acetyl-2-bromo-3-indolinone and 11.2 g of ethyl imidazole-2-carboxylate is heated for 15 minutes at 120° C. and, after cooling to 20° C., chromatographed on 1 kg of neutral silica gel (0.040–0.063 mm) contained in a column with a diameter of 10 cm, elution being carried out under pressure with a dichloromethane/ethyl acetate (60/40 by volume mixture 500 ml fractions being collected. Fractions 11 to 16 are combined and concentrated to dryness under reduced pressure (5 mm Hg; 0.65 kPa) at 50° C. The product obtained (9 g) is suspended in 100 ml of petroleum ether, filtered, washed with 20 ml of petroleum ether and dried under reduced pressure (5 mm Hg; 0.65 kPa) at 60° C. There are thus obtained 8.6 g of ethyl 1-(1-acetyl-3-oxo-2-indolinyl)imidazole-2-carboxylate, melting at 210° C.

1-Acetyl-2-bromo-3-indolineone can be prepared as described by V. S. Velezheva et al., Khim. Farm. Zh., 24(12), 46 (1990).

The medicaments according to the invention consist of a compound of formula (I) or a salt of such a compound, in the pure state or in the form of a composition in which it is combined with any other pharmaceutically compatible product, which can be inert or physiologically active. The medicaments according to the invention can be used orally, parenterally, rectally or topically.

Tablets, pills, powders (gelatin capsules or cachets) or granules can be used as solid compositions for oral administration. In these compositions, the active principle according to the invention is mixed with one or a number of inert diluents, such as starch, cellulose, sucrose, lactose or silica, under a stream or argon. These compositions can also comprise substances other than the diluents, for example one or a number of lubricating agents such as magnesium stearate or talc, a colouring agent, a coating (dragées) or a varnish.

Pharmaceutically acceptable solutions, suspensions, emulsions, syrups and elixirs containing inert diluents such as water, ethanol, glycerol, vegetable oils or paraffin oil can be used as liquid compositions for oral administration. These compositions can comprise substances other than the diluents, for example wetting, sweetening, thickening, flavouring or stabilizing substances.

The sterile compositions for parenteral administration can preferably be suspensions, emulsions or aqueous or non-aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which contain, besides the active product, excipients such as cocoa butter, semi-synthetic glycerides or poly(ethylene glycol)s.

The compositions for topical administration can be, for example, creams, lotions, eye drops, mouth washes, nose drops or aerosols.

In human therapeutics, the compounds according to the invention are particularly useful for the treatment and/or the prevention of conditions which require the administration of an antagonist of the AMPA receptor or of an antagonist of the NMDA receptor. These compounds are especially useful for treating or preventing all ischaemias and in particular cerebral ischaemia, the effects due to anoxia, the development of neurodegenerative diseases, Huntington's chorea, Alzheimer's disease, amyotrophic lateral sclerosis, olivopontocerebellar atrophy and Parkinson's disease, with respect to epileptogenic and/or convulsive symptoms, for the treatment of cerebral and spinal traumas, traumas related to generation of the inner ear or of the retina, anxiety, depression, schizophrenia, Tourette's syndrome or hepatic encephalopathy, as analgesics, antiinflammatories, antianorexics, antimigraines or antiemetics and for treating poisonings by neurotoxins or other agonist substances of the NMDA receptor, as well as the neurological disorders associated with viral diseases such as AIDS, rabies, measles and tetanus. These compounds are also useful for preventing symptoms of withdrawal from drugs and from alcohol and inhibiting addiction to and dependence on opiates as well as in the treatment of deficiencies related to mitochondrial anomalies such as mitochondrial myopathy, Leber's syndrome, Wernicke's encephalopathy, Rett's syndrome, homocysteinaemia, hyperprolinaemia, hydroxybutiricaminoaciduria, lead encephalopathy and sulphite oxidase deficiency.

The doses depend on the desired effect, on the duration of treatment and on the administration route used; they are generally between 10 mg and 100 mg per day orally for an adult with unit doses ranging from 5 mg to 50 mg of active substance.

Generally, the doctor will determine the appropriate dosage depending on the age, weight and all the other factors specific to the subject to be treated.

The following examples illustrate compositions according to the invention:

EXAMPLE A

Gelatin capsules containing 50 mg of active product are prepared, according to the usual technique, which have the following composition:

| Compound of formula (I) | 50 mg |
|---|---|
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg of active product are prepared, according to the usual technique, which have the following composition:

| Compound of formula (1) | 50 mg |
|---|---|
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) q.s. 1 coated tablet completed to | 245 mg |

EXAMPLE C

An injectable solution containing 10 mg of active product is prepared which has the following composition:

| Compound of formula (I) | 10 mg |
|---|---|
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water | q.s. 4 ml |

We claim:

1. A compound of formula (I) or a salt thereof:

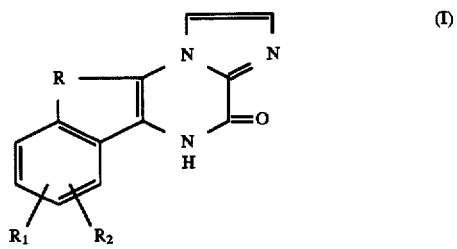

in which

R represents an oxygen or sulphur atom, or an NH or N-alk radical, $R_1$ and $R_2$, which are identical or different, each represents hydrogen, a halogen atom, an alkyl, alkoxy, amino, acylamino, —NH—CO—NH—Ar, —NlCH—N(alk)alk', nitro, cyano, phenyl, imidazolyl or $SO_3H$ radical, Ar represents a phenyl radical, said alkyl and alkoxy radicals containing from 1 to 4 carbon atoms in a straight or branched chain, and said acyl portions containing from 2 to 5 carbon atoms;

including isomers or mixtures of isomers of the compounds of formula (I) when $R_1$ and/or $R_2$ represent an —NlCH—N(alk)alk' radical.

2. A compound of formula (I) according to claim 1, in which $R_1$ and $R_2$ each represent a hydrogen atom and R represents an oxygen atom, a sulphur atom, or an NH or N-alk radical.

3. A pharmaceutical composition comprising an effective amount of a compound of formula (I) according to claim 1 and a pharmaceutically compatible carrier.

4. A pharmaceutical composition for antagonizing an AMPA receptor, which comprises an effective amount of a compound of formula (I) according to claim 1 and a pharmaceutically compatible carrier.

5. A pharmaceutical composition for antagonizing a NMDA receptor, which comprises an effective amount of a compound of formula (I) according to claim 1 and a pharmaceutically compatible carrier.

* * * * *

UNITED STATES PATENT AND TRADEMARK OFFICE
CERTIFICATE OF CORRECTION

PATENT NO. : 5,672,705
DATED : September 30, 1997
INVENTOR(S) : Jean-Claude ALOUP et al.

It is certified that error appears in the above-indentified patent and that said Letters Patent is hereby corrected as shown below:

Claim 1, column 11, line 3, "-N1CH-" should read -- -N=CH- --.

Claim 1, column 11, line 11, "-N1CH-N(alk)alk'" should read -- -N=CH-N(alk)alk'--.

Signed and Sealed this

Twenty-eighth Day of July, 1998

Attest:

BRUCE LEHMAN

*Attesting Officer*    Commissioner of Patents and Trademarks